United States Patent [19]

Fullerton

[11] 4,254,219

[45] Mar. 3, 1981

[54] PROCESS FOR RECORDING DATA IN THE LEUCOCYTE MIGRATION INHIBITION ASSAY

[75] Inventor: W. Wardle Fullerton, King of Prussia, Pa.

[73] Assignee: Merck & Co., Inc., Rahway, N.J.

[21] Appl. No.: 77,690

[22] Filed: Sep. 21, 1979

[51] Int. Cl.³ .............................................. C12Q 1/66
[52] U.S. Cl. ..................................... 435/7; 23/230 B; 424/3; 424/8; 424/12
[58] Field of Search ..................... 435/7; 424/12, 3, 8; 23/230 B

[56] References Cited

U.S. PATENT DOCUMENTS

| | | | |
|---|---|---|---|
| 3,960,489 | 6/1976 | Giaever | 23/230 B |
| 3,960,490 | 6/1976 | Giaever | 23/230 B |

OTHER PUBLICATIONS

J. E. Clausen, "Leukocyte Migration Inhibitory Factor", Manual of Clinical Immunology, Rose & Friedman Editors, American Soc. for Microbiology, pp. 100-105 (1976).

*Primary Examiner*—Robert J. Warden
*Attorney, Agent, or Firm*—Donald J. Perrella; Julian S. Levitt

[57] ABSTRACT

A method of detecting and quantitating the migration of leucocytes in agar gel by (1) fixing the cells; (2) staining them with Ponceau S or a similar dye; (3) destaining; and (4) dissolving the gel by gentle heating in the destaining solution. The stained cells remain adhered to the glass surface of the culture dish, and the cells can be read through a projection microscope or photographed for a permanent record.

6 Claims, No Drawings

PROCESS FOR RECORDING DATA IN THE LEUCOCYTE MIGRATION INHIBITION ASSAY

RELATIONSHIP TO THE PRIOR ART

In recent years, antigen-induced migration inhibition of leucocytes has become used extensively as an in vitro parameter of cell-mediated immunity in humans. One assay is a direct migration of leucocytes in an agar medium. Leucocytes are mixed with an antigen-containing medium, and an appropriate amount of the mixture added to holes punched in the agar medium in plates. During incubation, migration of the leucocytes through a capillary cleft beneath the gel will occur. At termination, the migration areas around the holes are studied and measured. See J. E. Clausen in *Manual of Clinical Immunology* (1976), pp. 100–105, "Leukocyte Migration Inhibitory Factor", Rose & Friedman, ed., published by American Society for Microbiology, for more details on the assay procedure.

SUMMARY OF THE INVENTION

This invention provides a process for permitting quantitating the leucocytes by providing a permanent record of the migration patterns. Although the migration patterns have always been apparent to a trained observer, it has not been easy to photograph the tracks, due to the optics of the gel. It has now been found that a sequence of steps involving fixing the cells, staining with Ponceau S or other protein stains or by using carbohydrate or nucleic acid stains, destaining and dissolution of the gel results in the fixation of the leucocytes to the glass plate, rendering them readily available for easy observation through a projection microscope or for permanent recordation by photography.

The steps involved in this process are first, fixing and staining. Most conveniently, these two procedures are combined by using a fixing and staining solution of 0.2% Ponceau S in 5% trichloroacetic acid (in water). This stain is a protein stain, and other suitable protein staining and/or fixing solutions are the following:

A. 0.001–0.002% Nigrosin in 2% acetic acid. Destain with water.
B. 0.2% Naphthalene Black in methanol:glacial acetic acid (9:1 v/v). Destain with 10% acetic acid in methanol.
C. 0.2% Amido Black in 5% acetic acid. Destain with 5% acetic acid.
D. 0.2% Light Green in 5% acetic acid. Destain with 5% acetic acid.
E. Coomassie Brilliant Blue R-250 (1.25 grams in mixture of 4.54 ml of 50% methanol and 46 ml of glacial acetic acid and filtered through Whatman No. 1 filter paper). Destain with a mixture of 75 ml glacial acetic acid, 50 ml methanol and 875 ml of water.

Other stains suitable to dye and fix the leucocytes are those which fix nucleic acid, proteins, or conjugated proteins, and which would fix those components of the leucocytes. For instance, the following procedure can be used:

Fix in 25% 2-propanol for 60 minutes. Place in a previously prepared solution of 5 ml of 0.1% (v/v) carbocyanine in formamide plus 20 ml formamide plus 100 ml 2-propanol plus 275 ml 15 mM trishydroxylmethoamino methane; adjusted to pH 8.5 overnight in the dark. Destain with 10% 2-propanol.

Another group of stains are those which fix glycoproteins (carbohydrate group). For instance, these are two methods:

A. 0.1% Alcian Blue 8GS in 0.05 M citrite buffer (pH 3.0) in 50% aqueous ethanol. Final pH 3.9. Destain with methanol containing 10% acetic acid.
B. Fix in 12.5% trichloroacetic acid for 60 minutes. Rinse with water. Place in 1% periodic acid for 60 minutes. Rinse with water. Place in 0.5% potassium metabisulphite for 60 minutes. Rinse with water. Place in 0.5% Alcian Blue 8GX in 3% acetic acid for 30 minutes. Destain with 5% acetic acid.

Fixing and staining solutions are allowed to react about 10–24 hours, preferably 14–16 hours.

Next, the plates are washed, suitably on a volume basis of acetic acid, methanol and water (7.5/5.0/87.5) once, or twice. The plates are covered with this solvent system (or a similar one) and then heated to 50°–60° C. for 2–3 hours. The gel is then loosened, and can be removed by shaking and washing and rinsing, with the same solvent system. The plates can then be viewed and photographed easily, or scanned in a spectrodensitometer.

A detailed example follows:

EXAMPLE 1

Medium O (32.5 ml) and horse serum (5.0 ml) are brought to 37° C. and added to 5% Agarose (12.5 ml) at 56° C. 2.5 ml of this mixture is added to a 54 mm diameter plastic dish and allowed to cool for 15–20 minutes. After cooling, 4–6 holes are punched in the agar with a ball point pen.

5 $\mu$l of white blood cells ($3 \times 10^8$ per ml) which have been incubated with the antigen (1 hour at 37° C.), are added to each hole in the agar. The plates are covered and placed in a $CO_2$ (3–4%) incubator overnight at 37° C. The plates are cooled for 15–20 minutes to room temperature. They are fixed and stained in one operation by covering with 0.2% Ponceau S in 5% trichloroacetic acid (in $H_2O$). After fixing and staining for 14–16 hours, the plates are washed several times with acetic acid/methanol/water (7.5/5.0/87.5). The additions are on a volume (ml) basis. After covering with the above solvent system, the plates (gels) are heated at 50°–60° C. for 2–3 hours. This loosens the gel, which is then shaken out. The plate is washed again with the above solvent system and is ready for viewing. The stained (pink) white blood cells are stuck on the bottom of the plate. The plates can be viewed by transmitted light and can be photographed or scanned in a spectrodensitometer. For photographing, one uses a Kodak Wratten gelatin green filter No. 54 with Polaroid black & white Type 105 or 665 film at F 4.5/1 using both transmitted and reflected light.

What is claimed is:

1. In an antigen-induced leucocyte migration assay wherein leucocytes are added to a hole in an agar medium, the improvement which comprises fixing and staining the leucocytes after formation of a precipitin band, and heating the system to permit removal of the agar medium.

2. The method of claim 1 wherein the stain is a protein stain.

3. The method of claim 2 in which the stain used is a staining and fixing solution of 0.2% Ponceau S in 5% trichloracetic acid in water.

4. The method of claim 1 wherein the system is washed before heating with a solvent system.

5. The method of claim 4 in which the washing solvent system is 7.5/5.0/87.5 acetic acid, methanol and water.

6. The method of claim 5 in which the heating is at 50°–60° C. for 2–3 hours.

* * * * *